(12) United States Patent  
Meier et al.

(10) Patent No.: US 9,403,894 B2  
(45) Date of Patent: Aug. 2, 2016

(54) GLUCAGON ANALOGUES

(75) Inventors: Eddi Meier, Vaerløse (DK); Ditte Riber, Brønshøj (DK); Jens Rosengren Daugaard, Virum (DK); Marie Skovgaard, Copenhagen Ø (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 13/702,841

(22) PCT Filed: Jun. 23, 2011

(86) PCT No.: PCT/DK2011/000067  
§ 371 (c)(1),  
(2), (4) Date: Feb. 25, 2013

(87) PCT Pub. No.: WO2011/160630  
PCT Pub. Date: Dec. 29, 2011

(65) Prior Publication Data  
US 2013/0157935 A1    Jun. 20, 2013

Related U.S. Application Data

(60) Provisional application No. 61/358,623, filed on Jun. 25, 2010.

(30) Foreign Application Priority Data

Jun. 23, 2010  (DK) ............................... 2010 00550

(51) Int. Cl.  
*C07K 14/605* (2006.01)  
*A61K 45/06* (2006.01)  
*A61K 38/26* (2006.01)

(52) U.S. Cl.  
CPC ............ *C07K 14/605* (2013.01); *A61K 38/26* (2013.01); *A61K 45/06* (2013.01)

(58) Field of Classification Search  
None  
See application file for complete search history.

(56) References Cited

U.S. PATENT DOCUMENTS

| | | | |
|---|---|---|---|
| 7,994,122 B2 | 8/2011 | Riber et al. | |
| 8,642,540 B2 | 2/2014 | Meier et al. | |
| 8,642,541 B2 | 2/2014 | Meier et al. | |
| 8,680,049 B2 | 3/2014 | Meier et al. | |
| 8,685,919 B2 | 4/2014 | Meier et al. | |
| 9,156,901 B2 | 10/2015 | Riber et al. | |
| 9,169,310 B2 | 10/2015 | Riber et al. | |
| 9,180,169 B2 | 11/2015 | Tolborg et al. | |
| 2005/0070469 A1 | 3/2005 | Bloom et al. | |
| 2010/0099601 A1 | 4/2010 | Weiss | |
| 2010/0190701 A1 | 7/2010 | Day et al. | |
| 2011/0286981 A1* | 11/2011 | Meier et al. | 424/93.21 |
| 2011/0286982 A1* | 11/2011 | Meier et al. | 424/93.21 |
| 2011/0293586 A1 | 12/2011 | Meier et al. | |
| 2011/0293587 A1 | 12/2011 | Meier et al. | |
| 2012/0178670 A1 | 7/2012 | Riber et al. | |
| 2013/0157929 A1 | 6/2013 | Riber et al. | |
| 2013/0157935 A1 | 6/2013 | Meier et al. | |
| 2013/0157953 A1* | 6/2013 | Petersen et al. | 514/11.7 |
| 2013/0316941 A1 | 11/2013 | Hamprecht et al. | |
| 2014/0011733 A1 | 1/2014 | Fosgerau et al. | |
| 2014/0080757 A1 | 3/2014 | Tolborg et al. | |
| 2014/0127174 A1 | 5/2014 | Meier et al. | |
| 2014/0127175 A1 | 5/2014 | Meier et al. | |
| 2015/0080295 A1 | 3/2015 | Meier et al. | |
| 2015/0111817 A1 | 4/2015 | Riber et al. | |
| 2015/0111826 A1 | 4/2015 | Riber et al. | |

FOREIGN PATENT DOCUMENTS

| | | |
|---|---|---|
| AU | 2008326324 A1 | 5/2009 |
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 2025684 A1 | 2/2009 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |

(Continued)

OTHER PUBLICATIONS

Abbrecht et al., "Erythrocyte life-span in mice acclimatized to different degrees of hypoxia," *J. Appl. Physiol.* 32:443-445, 1972.

Adelhorst et al., "Structure-activity studies of glucagon-like peptide-1," *J. Biol. Chem.* 269:6275-6278, 1994.

Altschul et al., "Local Alignment Statistics," *Methods in Enzymology* 266:460-480, 1996.

Authier et al., "Endosomal Proteolysis of Glucagon at Neutral pH generates the bioactive Degradation Product Miniglucagon-(19-29)," *Endocrinology* 144:5353-5364, 2003.

Blache et al., "Endopeptidase from Rat Liver Membranes, Which Generates Miniglucagon from Glucagon," *J. Biol. Chem.* 268:21748-21753, 1993.

Cavanaugh et al., "Isolation and Structural Characterization of Proglucagon-Derived Peptides, Pancreatic Polypeptide, and Somatostatin from the Urodele *Amphiuma tridactylum*," *Gen. Compar. Endocrin.* 101:12-20, 1996.

Chan et al., "Suppression of weight gain by glucagon in obese Zucker rats," *Exp. Mol. Path.* 40:320-327, 1984.

(Continued)

*Primary Examiner* — Brian J Gangle  
*Assistant Examiner* — Andrea McCollum  
(74) *Attorney, Agent, or Firm* — Clark & Elbing LLP; Kristina Bieker-Brady

(57) ABSTRACT

The invention provides materials and methods for promoting weight loss or preventing weight gain without affecting glycemic control. In particular, the invention provides novel glucagon analog peptides effective in such methods. The peptides may mediate their effect by having increased selectivity for the glucagon-like peptide-1 (GLP-1) receptor as compared to human glucagon.

22 Claims, 6 Drawing Sheets

(56) References Cited

FOREIGN PATENT DOCUMENTS

| WO | WO-2004/096854 A2 | 11/2004 |
|---|---|---|
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/100535 A2 | 9/2007 |
| WO | WO-2008/010101 A2 | 1/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/067636 A2 | 5/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/014946 A2 | 2/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2011/006497 A1 | 1/2011 |
| WO | WO-2011/088837 A1 | 7/2011 |
| WO | WO-2011/160630 A2 | 12/2011 |
| WO | WO-2011/160633 A1 | 12/2011 |
| WO | WO-2012/098462 A1 | 7/2012 |
| WO | WO-2013/092703 A2 | 6/2013 |
| WO | WO-2014/041195 A1 | 3/2014 |

OTHER PUBLICATIONS

Cohen et al., "Oxyntomodulin Suppresses Appetite and Reduces Food Intake in Humans," *Journal of Clinical Endocrinology & Metabolism* 88:4696-4701, 2003.
Dakin et al., "Oxyntomodulin Inhibits Food Intake in the Rat," *Endocrinology* 142:4244-4250, 2001.
Dakin et al., "Peripheral oxyntomodulin reduces food intake and body weight gain in rats," *Endocrinology* 145:2687-2695, 2004.
Day et al., "A new glucagon and GLP-1 co-agonist eliminates obesity in rodents," *Nat. Chem. Biol.* 5:749-757, 2009.
Delgado et al., "The uses and properties of PEG-linked proteins," *Crit. Rev. Ther. Drug. Carrier Syst.* 9:249-304, 1992.
Druce et al., "Investigation of structure-activity relationships of Oxyntomodulin (Oxm) using Oxm analogs," *Endocrinology* 150:1712-1721, 2009.
England et al., "Glucagon Carboxyl-Terminal Derivatives: Preparation, Purification and Characterization," *Biochemistry* 21:940-950, 1982.
Francis et al., "PEGylation of cytokines and other therapeutic proteins and peptides: the importance of biological optimisation of coupling techniques," *Int. J. Hematol.* 68:1-18, 1998.
Frandsen et al., "Glucagon: Structure-Function Relationships Investigated by Sequence Deletions," *Hoppe-Seyler's Z Physiol. Chem.* 362:665-677, 1981.
Gelfanov et al., "Discovery and structural optimization of high affinity co-agonists at the glucagon and GLP-1 receptors," *Understanding Biology Using Peptides*, ed. Sylvie E. Blondelle, American Peptide Society, 763-764, 2005.
Göke et al.,"Exendin-4 is a high potency agonist and truncated exendin-(9-39)-amide an antagonist at the glucagon-like peptide 1-(7-36)-amide receptor of insulin-secreting β-cells," *J. Biol. Chem.* 268:19650-19655, 1993.
Gombotz et al. "Biodegradable Polymers for Protein and Peptide Drug Delivery," *Bioconjugate Chem.* 6:332-351, 1995.
Hjorth et al., "Glucagon and Glucagon-Like Peptide 1: Selective Receptor Recognition Via Distinct Peptide Epitopes," *J. Biol. Chem.* 269:30121-30124, 1994.

Hruby et al., "The design and biological activities of glucagon agonists and antagonists, and their use in examining the mechanisms of glucose action," *Curr. Med. Chem.—Imm., Endoc. & Metab. Agents* 1:199-215, 2001.
Hudecz et al., "Synthesis, Conformation, Biodistribution, and in Vitro Cytotoxicity of Daunomycin-Branched Polypeptide Conjugates," *Bioconjugate Chem.* 3:49-57, 1992.
International Search Report for PCT/DK2011/000067 mailed Dec. 9, 2011.
Joshi et al., "The Estimation of Glutaminyl Deamidation and Aspartyl Cleavage Rates in Glucagon," *Int. J. Pharma.* 273:213-219, 2004.
Kallenbach et al., "Role of the Peptide Bond in Protein Structure and Folding " *The Amide Linkage*, Chapter 18, pp. 599-622, 2000.
Knudsen et al., "Potent Derivatives of Glucagon-like Peptide-1 with Pharmacokinetic Properties Suitable for Once Daily Administration," *J. Med. Chem.* 43:1664-1669, 2000.
Madsen et al., "Structure-activity and protraction relationship of long-acting glucagon-like peptide-1 derivatives: importance of fatty acid length, polarity, and bulkiness," *J. Med. Chem* 50:6126-6132, 2007.
McKee et al., "Receptor binding and adenylate cyclase activities of glucagon analogues modified in the N-terminal region," *Biochemistry* 25:1650-1656, 1986.
NCBI Genbank Accession No. 721913A, downloaded Dec. 15, 2009.
Pan et al, "Design of a long acting peptide functioning as both a glucagon-like peptide-1 receptor agonist and a glucagon receptor antagonist," *J. Biol. Chem.* 281:12506-12515, 2006.
Parlevliet et al., "Oxyntomodulin ameliorates glucose intolerance in mice fed a high-fat diet," *Am. J. Physiol. Endocrinol. Metab.* 294:E142-E147, 2008.
Pratesi et al., "Poly-L-aspartic acid as a carrier for doxorubicin: a comparative in vivo study of free and polymer-bound drug," *Br. J. Cancer* 52:841-848, 1985.
Tsukada et al., "An anti-α-fetoprotein antibody-daunorubicin conjugate with a novel poly-L-glutamic acid derivative as intermediate drug carrier," *J. Natl. Cancer Inst.* 73:721-729, 1984.
Unson et al., "Glucagon antagonists: contribution to binding and activity of the amino-terminal sequence 1-5, position 12, and the putative α-helical segment 19-27," *J. Biol. Chem.* 264(2):789-794, 1989.
Unson et al., "Identification of an essential serine residue in glucagon: implication for an active site triad," *Proc. Natl. Acad. Sci. U.S.A.* 91:454-458, 1994.
Unson et al., "Positively charged residues at positions 12, 17, and 18 of glucagon ensure maximum biological potency," *J. Biol. Chem.* 273:10308-10312, 1998.
Zalipsky, "Functionalized poly(ethylene glycol) for preparation of biologically relevant conjugates," *Bioconjugate Chem.* 6:150-165, 1995.
Zhu et al.,"The Role of Dipeptidyl Peptidase IV in the Cleavage of Glucagon Family Peptides: In Vivo Metabolism of Pituitary Adenylate Cyclase Activating Polypeptide-(1-38)," *J. Biol. Chem.* 278:22418-22423, 2003.
Jaya et al., "Mechanism of hypocholesterolemic action of glucagon." J Biosci. 12(2):111-4 (1987).
Hostrup et al., Modification of Peptides and Proteins. *Delivery Technologies for Biopharmaceuticals: Peptides, Proteins, Nucleic Acids and Vaccines*. Wiley & Sons, 171-91 (2009).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Written Opinion for Singapore Application No. 201209089-0 dated Nov. 8, 2013 (10 pages).
U.S. Appl. No. 14/195,533, Meier et al.
U.S. Appl. No. 14/516,216, Riber et al.
U.S. Appl. No. 14/517,497, Riber et al.
Wermuth et al., "Glossary of terms used in medicinal chemistry," Pure & Appl Chem. 70(5):1129-43 (1998).
Communication from the European Patent Office for European Patent Application No. 08 875 673.9-2405 dated Jul. 4, 2012 (6 pages).

(56) References Cited

OTHER PUBLICATIONS

European Search Report from European Patent Application No. 07016032.0, completed Jan. 28, 2008 (8 pages).
International Search Report for PCT/DK2010/000099, mailed Dec. 2, 2010 (2 pages).
International Search Report for PCT/GB2008/002041, mailed Sep. 9, 2008 (3 pages).
International Search Report for PCT/GB2008/004157, mailed Jun. 4, 2009 (21 pages).
International Search Report and Written Opinion for PCT/GB2008/004121, mailed Jun. 30, 2009 (25 pages).
International Search Report and Written Opinion for PCT/GB2008/004130, mailed Mar. 25, 2009 (17 pages).
International Search Report and Written Opinion for PCT/GB2008/004132 mailed Jun. 10, 2009 (16 pages).
International Search Report for PCT/DK2011/000072, mailed Dec. 6, 2011 (3 pages).
International Search Report for International Application No. PCT/IB2012/000134, mailed Jun. 25, 2012 (3 pages).
International Preliminary Report on Patentability for PCT/GB2008/002041, issued Dec. 17, 2009 (7 pages).
Protest of U.S. Appl. No. 12/664,534 Pursuant 37 CFR 1.291, mailed Jan. 13, 2010 (14 pages).
U.S. Appl. No. 14/843,047, Zealand Pharma A/S.
U.S. Appl. No. 14/853,335, Zealand Pharma A/S.
U.S. Appl. No. 14/857,067, Zealand Pharma A/S.
Ali et al., "Cardiomyocyte glucagon receptor signaling modulates outcomes in mice with experimental myocardial infarction," Mol Metab. 4(2):132-143 (2015).
Fang et al., "Diabetic cardiomyopathy: evidence, mechanisms, and therapeutic implications," Endocr Rev. 25(4):543-67 (2004).
International Preliminary Report on Patentability for PCT/EP2013/069286, completed Jan. 19, 2015 (40 pages).
International Search Report and Written Opinion for PCT/EP2013/069286, mailed Dec. 18, 2013 (16 pages).
Mehta, "Diabetic cardiomyopathy: insights into pathogenesis, diagnostic challenges, and therapeutic options," Intl J Pharm Sci Res. 3(10):3565-3576 (2012).
Pocai, "Glucagon signaling in the heart: activation or inhibition?," Mol Metab. 4(2):81-2 (2015).
Rose et al., "Insulin proteinase liberates from glucagon a fragment known to have enhanced activity against $Ca^{2+} + Mg^{2+}$-dependent ATPase," Biochem J. 256(3):847-51 (1988).
Written Opinion for PCT/DK2011/000072, mailed Dec. 6, 2011 (6 pages).

\* cited by examiner

SEQUENCE LISTING

```
<160> NUMBER OF SEQ ID NOS: 17

<210> SEQ ID NO 1
<211> LENGTH: 29
<212> TYPE: PRT
<213> ORGANISM: Artificial
<220> FEATURE:
<223> OTHER INFORMATION: Synthetic peptide sequence

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 8
<212> TYPE: PRT
<213> ORGANISM: Artificial
<220> FEATURE:
<223> OTHER INFORMATION: Synthetic peptide sequence
```

-continued

```
<400> SEQUENCE: 2

Lys Arg Asn Arg Asn Asn Ile Ala
1               5

<210> SEQ ID NO 3
<211> LENGTH: 37
<212> TYPE: PRT
<213> ORGANISM: Artificial
<220> FEATURE:
<223> OTHER INFORMATION: Synthetic peptide sequence

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 4
<211> LENGTH: 29
<212> TYPE: PRT
<213> ORGANISM: Artificial
<220> FEATURE:
<223> OTHER INFORMATION: Synthetic peptide sequence

<400> SEQUENCE: 4

His Ser Gln Gly Thr Phe Thr Ser Asp Tyr Ser Lys Tyr Leu Asp Glu
1               5                   10                  15

Arg Arg Ala Lys Asp Phe Ile Glu Trp Leu Leu Ser Ala
            20                  25

<210> SEQ ID NO 5
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (27)..(27)
<223> OTHER INFORMATION: Xaa = K(HEXADECANOYL-ISOGLU)

<400> SEQUENCE: 5

His Ser Gln Gly Thr Phe Thr Ser Asp Tyr Ser Lys Tyr Leu Asp Glu
1               5                   10                  15

Arg Arg Ala Lys Asp Phe Ile Glu Trp Leu Xaa Ser Ala
            20                  25

<210> SEQ ID NO 6
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (20)..(20)
<223> OTHER INFORMATION: Xaa = K(HEXADECANOYL-ISOGLU)

<400> SEQUENCE: 6

His Ser Gln Gly Thr Phe Thr Ser Asp Tyr Ser Lys Tyr Leu Asp Glu
1               5                   10                  15

Arg Arg Ala Xaa Asp Phe Ile Glu Trp Leu Leu Ser Ala
```

```
        20                  25

<210> SEQ ID NO 7
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = K(HEXADECANOYL-ISOGLU)

<400> SEQUENCE: 7

His Ser Gln Gly Thr Phe Thr Ser Asp Tyr Ser Lys Tyr Leu Asp Glu
1               5                   10                  15

Arg Arg Ala Lys Asp Phe Ile Glu Trp Leu Leu Xaa Ala
            20                  25

<210> SEQ ID NO 8
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (16)..(16)
<223> OTHER INFORMATION: Xaa = K(HEXADECANOYL-ISOGLU)

<400> SEQUENCE: 8

His Ser Gln Gly Thr Phe Thr Ser Asp Tyr Ser Lys Tyr Leu Asp Xaa
1               5                   10                  15

Arg Arg Ala Lys Asp Phe Ile Glu Trp Leu Leu Ser Ala
            20                  25

<210> SEQ ID NO 9
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (17)..(17)
<223> OTHER INFORMATION: Xaa = K(HEXADECANOYL-ISOGLU)

<400> SEQUENCE: 9

His Ser Gln Gly Thr Phe Thr Ser Asp Tyr Ser Lys Tyr Leu Asp Glu
1               5                   10                  15

Xaa Arg Ala Lys Asp Phe Ile Glu Trp Leu Leu Ser Ala
            20                  25

<210> SEQ ID NO 10
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (17)..(17)
<223> OTHER INFORMATION: Xaa = K(Hexadecanoyl-isoGlu)

<400> SEQUENCE: 10
```

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Leu Ser Ala
            20                  25

<210> SEQ ID NO 11
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa is selected from Ser and Aib
<220> FEATURE:
<221> NAME/KEY: MISC_FEATURE
<222> LOCATION: (16)..(16)
<223> OTHER INFORMATION: Xaa is selected from Glu and Lys, Cys or Orn
<220> FEATURE:
<221> NAME/KEY: MISC_FEATURE
<222> LOCATION: (17)..(17)
<223> OTHER INFORMATION: Xaa is selected from Arg and Lys, Cys or Orn
<220> FEATURE:
<221> NAME/KEY: MISC_FEATURE
<222> LOCATION: (20)..(20)
<223> OTHER INFORMATION: Xaa is selected from Lys and Cys or Orn
<220> FEATURE:
<221> NAME/KEY: MISC_FEATURE
<222> LOCATION: (24)..(24)
<223> OTHER INFORMATION: Xaa is selected from Glu and Lys, Cys or Orn
<220> FEATURE:
<221> NAME/KEY: MISC_FEATURE
<222> LOCATION: (27)..(27)
<223> OTHER INFORMATION: Xaa is selected from Leu and Lys, Cys or Orn
<220> FEATURE:
<221> NAME/KEY: MISC_FEATURE
<222> LOCATION: (28)..(28)
<223> OTHER INFORMATION: Xaa is selected from Ser and Lys, Cys, Orn or
      absent
<220> FEATURE:
<221> NAME/KEY: MISC_FEATURE
<222> LOCATION: (29)..(29)
<223> OTHER INFORMATION: Xaa is Ala or absent

<400> SEQUENCE: 11

His Xaa Gln Gly Thr Phe Thr Ser Asp Tyr Ser Lys Tyr Leu Asp Xaa
1               5                   10                  15

Xaa Arg Ala Xaa Asp Phe Ile Xaa Trp Leu Xaa Xaa Xaa
            20                  25

<210> SEQ ID NO 12
<211> LENGTH: 29
<212> TYPE: PRT
<213> ORGANISM: Artificial
<220> FEATURE:
<223> OTHER INFORMATION: Synthetic peptide sequence

<400> SEQUENCE: 12

His Ser Gln Gly Thr Phe Thr Ser Asp Tyr Ser Lys Tyr Leu Asp Glu
1               5                   10                  15

Arg Arg Ala Lys Asp Phe Ile Glu Trp Leu Lys Ser Ala
            20                  25

<210> SEQ ID NO 13
<211> LENGTH: 29
<212> TYPE: PRT
<213> ORGANISM: Artificial
<220> FEATURE:
<223> OTHER INFORMATION: Synthetic peptide sequence

```
<400> SEQUENCE: 13

His Ser Gln Gly Thr Phe Thr Ser Asp Tyr Ser Lys Tyr Leu Asp Glu
1               5                   10                  15

Arg Arg Ala Lys Asp Phe Ile Glu Trp Leu Leu Ser Ala
            20                  25

<210> SEQ ID NO 14
<211> LENGTH: 29
<212> TYPE: PRT
<213> ORGANISM: Artificial
<220> FEATURE:
<223> OTHER INFORMATION: Synthetic peptide sequence

<400> SEQUENCE: 14

His Ser Gln Gly Thr Phe Thr Ser Asp Tyr Ser Lys Tyr Leu Asp Glu
1               5                   10                  15

Arg Arg Ala Lys Asp Phe Ile Glu Trp Leu Leu Lys Ala
            20                  25

<210> SEQ ID NO 15
<211> LENGTH: 29
<212> TYPE: PRT
<213> ORGANISM: Artificial
<220> FEATURE:
<223> OTHER INFORMATION: Synthetic peptide sequence

<400> SEQUENCE: 15

His Ser Gln Gly Thr Phe Thr Ser Asp Tyr Ser Lys Tyr Leu Asp Lys
1               5                   10                  15

Arg Arg Ala Lys Asp Phe Ile Glu Trp Leu Leu Ser Ala
            20                  25

<210> SEQ ID NO 16
<211> LENGTH: 29
<212> TYPE: PRT
<213> ORGANISM: Artificial
<220> FEATURE:
<223> OTHER INFORMATION: Synthetic peptide sequence

<400> SEQUENCE: 16

His Ser Gln Gly Thr Phe Thr Ser Asp Tyr Ser Lys Tyr Leu Asp Glu
1               5                   10                  15

Lys Arg Ala Lys Asp Phe Ile Glu Trp Leu Leu Ser Ala
            20                  25

<210> SEQ ID NO 17
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 17

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Leu Ser Ala
            20                  25
```

GLUCAGON ANALOGUES

CROSS-REFERENCE TO RELATED APPLICATIONS

This application claims priority under 35 U.S.C. §371 from International Application No. PCT/DK2011/000067, filed on Jun. 23, 2011, which claims benefit of Danish Application No. PA 2010 00550, filed on Jun. 23, 2010 and U.S. Provisional Application No. 61/358,623, filed on Jun. 25, 2010.

FIELD OF THE INVENTION

The present invention relates to glucagon analogues and their medical use, for example in the treatment of excess food intake, obesity and excess weight, elevated cholesterol, and with no or only little effect on glycemic control.

BACKGROUND OF THE INVENTION

Preproglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1). Oxyntomodulin (OXM) is a 37 amino acid peptide which includes the complete 29 amino acid sequence of glucagon with an octapeptide carboxyterminal extension (amino acids 82 to 89 of pre-proglucagon, having the sequence Lys-Arg-Asn-Arg-Asn-Asn-Ile-Ala (SEQ ID NO: 2) and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala) (SEQ ID NO: 3). The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia.

OXM is released into the blood in response to food ingestion and in proportion to meal calorie content. OXM has been shown to suppress appetite and inhibit food intake in humans (Cohen et al, Journal of Endocrinology and Metabolism, 88, 4696-4701, 2003; WO 2003/022304). In addition to those anorectic effects, which are similar to those of GLP-1, OXM must also affect body weight by another mechanism, since rats treated with oxyntomodulin show less body weight gain than pair-fed rats (Bloom, Endocrinology 2004, 145, 2687). Treatment of obese rodents with OXM also improves their glucose tolerance (Parlevliet et al, Am J Physiol Endocrinol Metab, 294, E142-7, 2008) and suppresses body weight gain (WO 2003/022304).

OXM activates both the glucagon and the GLP-1 receptors with a two-fold higher potency for the glucagon receptor over the GLP-1 receptor, but is less potent than native glucagon and GLP-1 on their respective receptors. Human glucagon is also capable of activating both receptors, though with a strong preference for the glucagon receptor over the GLP-1 receptor. GLP-1 on the other hand is not capable of activating glucagon receptors. The mechanism of action of oxyntomodulin is not well understood. In particular, it is not known whether some of the extrahepatic effects of the hormone are mediated through the GLP-1 and glucagon receptors, or through one or more unidentified receptors.

Other peptides have been shown to bind and activate both the glucagon and the GLP-1 receptor (Hjort et al, Journal of Biological Chemistry, 269, 30121-30124, 1994) and to suppress body weight gain and reduce food intake (WO 2006/134340, WO 2007/100535, WO 2008/10101, WO 2008/152403, WO 2009/155257 and WO 2009/155258).

Obesity is a globally increasing health problem is associated with various diseases, particularly cardiovascular disease (CVD), type 2 diabetes, obstructive sleep apnea, certain types of cancer, and osteoarthritis. As a result, obesity has been found to reduce life expectancy. According to 2005 projections by the World Health Organization there are 400 million adults (age>15) classified as obese worldwide. In the US, obesity is now believed to be the second-leading cause of preventable death after smoking.

The rise in obesity drives an increase in diabetes, and approximately 90% of people with type 2 diabetes may be classified as obese. There are 246 million people worldwide with diabetes, and by 2025 it is estimated that 380 million will have diabetes. Many have additional cardiovascular risk factors, including high/aberrant LDL and triglycerides and low HDL.

Accordingly, there is a strong medical need for treating obesity.

SUMMARY OF THE INVENTION

The invention provides a compound having the formula

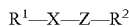

wherein $R^1$ is H, $C_{1-4}$ alkyl, acetyl, formyl, benzoyl or trifluoroacetyl;

$R^2$ is OH or $NH_2$;

X is a peptide which has the formula I:

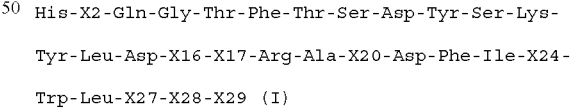

wherein
X2 is selected from Ser and Aib;
X16 is selected from Glu and Y;
X17 is selected from Arg and Y;
X20 is selected from Lys and Y;
X24 is selected from Glu and Y;
X27 is selected from Leu and Y;
X28 is selected from Ser and Y or absent;
X29 is Ala or absent;
wherein at least one of X16, X17, X20, X24, X27 and X28 is Y;
wherein each residue Y is independently selected from Lys, Cys and Orn;

wherein the side chain of at least one amino acid residue Y of X is conjugated to a lipophilic substituent having the formula:

(i) $Z^1$, wherein $Z^1$ is a lipophilic moiety conjugated directly to the side chain of X; or (ii) $Z^1Z^2$, wherein $Z^1$ is a lipophilic moiety, $Z^2$ is a spacer, and $Z^1$ is conjugated to the side chain of X via $Z^2$;

and Z is absent or is a sequence of 1-20 amino acid units independently selected from the group consisting of Ala, Leu, Ser, Thr, Tyr, Cys, Glu, Lys, Arg, Dbu, Dpr and Orn;

or a pharmaceutically acceptable salt thereof.

In one example, X may have the sequence:

```
                                      (SEQ ID NO: 12)
HSQGTFTSDYSKYLDERRAKDFIEWLKSA (SEQ ID NO: 13)
HSQGTFTSDYSKYLDERRAKDFIEWLLSA (SEQ ID NO: 14)
HSQGTFTSDYSKYLDERRAKDFIEWLLKA (SEQ ID NO: 15)
HSQGTFTSDYSKYLDKRRAKDFIEWLLSA (SEQ ID NO: 16)
HSQGTFTSDYSKYLDEKRAKDFIEWLLSA
or (SEQ ID NO: 17)
H-Aib-QGTFTSDYSKYLDEKRAKDFIEWLLSA
```

In some embodiments, the lipophilic substituent is attached to the amino acid residue at position 16, 17, 20, 27 or 28.

For example, the compound of the invention may have the sequence:

```
                                      (SEQ ID NO: 5)
H-HSQGTFTSDYSKYLDERRAKDFIEWL-K(Hexadecanoyl-
isoGlu)-SA-NH2

(SEQ ID NO: 6)
H-HSQGTFTSDYSKYLDERRA-K(Hexadecanoyl-isoGlu)-
DFIEWLLSA-NH2

(SEQ ID NO: 7)
H-HSQGTFTSDYSKYLDERRAKDFIEWLL-K(Hexadecanoyl-
isoGlu)-A-NH2

(SEQ ID NO: 8)
H-HSQGTFTSDYSKYLD-K(Hexadecanoyl-isoGlu)-
RRAKDFIEWLLSA-NH2

(SEQ ID NO: 9)
H-HSQGTFTSDYSKYLDE-K(Hexadecanoyl-isoGlu)-
RAKDFIEWLLSA-NH
or (SEQ ID NO: 10)
H-H-Aib-QGTFTSDYSKYLDE-K(Hexadecanoyl-isoGlu)-
RAKDFIEWLLSA-NH2
```

The invention further provides a nucleic acid (which may be DNA or RNA) encoding a compound of the invention, an expression vector comprising such a nucleic acid, and a host cell containing such a nucleic acid or expression vector.

In a further aspect, the present invention provides a composition comprising a glucagon analogue peptide as defined herein, or a salt or derivative thereof, a nucleic acid encoding such a glucagon analogue peptide, an expression vector comprising such a nucleic acid, or a host cell containing such a nucleic acid or expression vector, in admixture with a carrier.

In preferred embodiments, the composition is a pharmaceutically acceptable composition and the carrier is a pharmaceutically acceptable carrier. The glucagon peptide analogue may be in the form of a pharmaceutically acceptable salt of the glucagon analogue.

In still a further aspect, the present invention provides a composition for use in a method of medical treatment.

The compounds described find use, inter alia, in preventing weight gain or promoting weight loss. By "preventing" is meant inhibiting or reducing when compared to the absence of treatment, and is not necessarily meant to imply complete cessation of weight gain. The peptides may cause a decrease in food intake and/or increased energy expenditure, resulting in the observed effect on body weight. Independently of their effect on body weight, the compounds of the invention may have a beneficial effect on circulating cholesterol levels, being capable of lowering circulating LDL levels and increasing HDL/LDL ratio. Thus the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for the prevention of metabolic syndrome, hypertension, atherogenic dyslipidemia, atherosclerosis, arteriosclerosis, coronary heart disease, or stroke. Their effects in these conditions may be as a result of or associated with their effect on body weight, or may be independent thereof.

In certain embodiments, the compounds described may find use in preventing weight gain or promoting weight loss with no or only little effect on glycemic control. It has been found in the present invention that certain of the compounds described have marked effect on weight loss with no or only little effect on the HbA1c level in a well-established animal model.

As already described, the invention extends to expression vectors comprising the above-described nucleic acid sequence, optionally in combination with sequences to direct its expression, and host cells containing the expression vectors. Preferably the host cells are capable of expressing and secreting the compound of the invention. In a still further aspect, the present invention provides a method of producing the compound, the method comprising culturing the host cells under conditions suitable for expressing the compound and purifying the compound thus produced.

The invention further provides a nucleic acid of the invention, an expression vector of the invention, or a host cell capable of expressing and secreting a compound of the invention, for use in a method of medical treatment. It will be understood that the nucleic acid, expression vector and host cells may be used for treatment of any of the disorders described herein which may be treated with the compounds of the invention themselves. References to a therapeutic composition comprising a compound of the invention, administration of a compound of the invention, or any therapeutic use thereof, should therefore be construed to encompass the equivalent use of a nucleic acid, expression vector or host cell of the invention, except where the context demands otherwise.

DETAILED DESCRIPTION OF THE INVENTION

Figure 1:
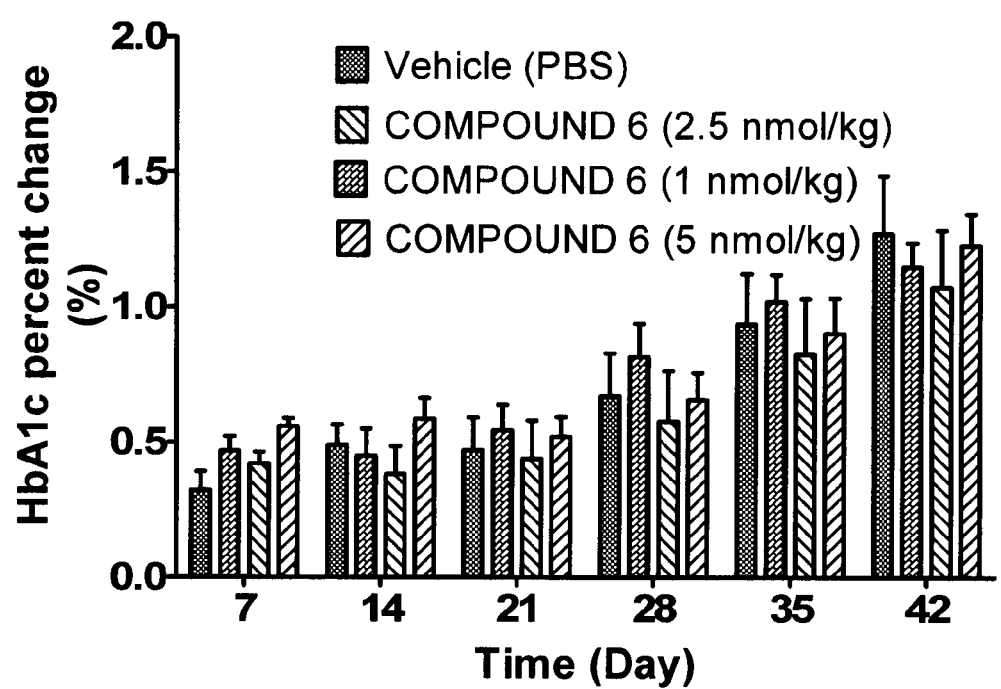
FIG. 1: Effect of s.c. administration of the Glu-GLP-1 dual agonist compound 6 on the change in HbA1c over the 6 weeks treatment period in db/db mice. Data are shown as mean+ SEM with n=11/group. *$p<0.05$, $p<0.01$, *$p<0.001$ compared to vehicle at the same time point.

Throughout this specification, the conventional one letter and three letter codes for naturally occurring amino acids are used, as well as generally accepted three letter codes for other amino acids, such as Aib (α-aminoisobutyric acid), Orn (ornithine), Dbu (2,4 diaminobutyric acid) and Dpr (2,3-diaminopropanoic acid).

The term "native glucagon" refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO: 1).

The invention provides compounds as defined above. For the avoidance of doubt, in the definitions provided herein, it is generally intended that the sequence of X only differs from Formula I at those positions which are stated to allow variation. Amino acids within the sequence X can be considered to be numbered consecutively from 1 to 29 in the conventional N-terminal to C-terminal direction. Reference to a "position" within X should be construed accordingly, as should reference to positions within native human glucagon and other molecules.

The compounds of the invention may carry one or more intramolecular bridge within the peptide sequence X. Each such bridge is formed between the side chains of two amino acid residues of X which are typically separated by three amino acids in the linear sequence of X (i.e. between amino acid A and amino acid A+4).

More particularly, the bridge may be formed between the side chains of residue pairs 12 and 16, 16 and 20, 17 and 21, 20 and 24, or 24 and 28. The two side chains can be linked to one another through ionic interactions, or by covalent bonds. Thus these pairs of residues may comprise oppositely charged side chains in order to form a salt bridge by ionic interactions. For example, one of the residues may be Glu or Asp, while the other may be Lys or Arg. The pairs Lys and Glu and Lys and Asp, respectively, may also be capable of reacting to form a lactam ring. Likewise, a Tyr and a Glu or a Tyr and an Asp are capable of forming a lactone ring.

Without wishing to be bound by any particular theory, it is believed that such intramolecular bridges stabilise the alpha helical structure of the molecule and thereby increase potency and/or selectivity at the GLP-1 receptor and possibly also the glucagon receptor.

Without wishing to be bound by any particular theory, the arginine residues at positions 17 and 18 of native glucagon appear to provide significant selectivity for the glucagon receptor Without wishing to be bound by any particular theory, the residues at positions 27, 28 and 29 of native glucagon appear to provide significant selectivity of the peptide for the glucagon receptor. Substitutions at one, two or all three of these positions with respect to the native glucagon sequence may increase potency at and/or selectivity for the GLP-1 receptor, potentially without significant reduction of potency at the glucagon receptor. Particular examples include Leu at position 27, Ser at position 28 and Ala at position 29.

Substitution of the naturally-occurring Met residue at position 27 (e.g. with Leu or Lys, especially with Leu) also reduces the potential for oxidation, thereby increasing the chemical stability of the compounds.

Substitution of the naturally-occurring Asn residue at position 28 (e.g. by Ser, Arg or Ala) also reduces the potential for deamidation in acidic solution, so increasing the chemical stability of the compounds.

Potency and/or selectivity at the GLP-1 receptor may also be increased by introducing residues that are likely to form an amphipathic helical structure, potentially without significant loss of potency at the glucagon receptor. This may be achieved by introduction of charged residues at one or more of positions 16, 20, 24, and 28. Thus the residues at positions 16 and 20 may both be charged, the residues at positions 16 and 24 may both be charged, the residues at positions 20 and 24 may both be charged, the residues at positions 16, 20 and 24 may all be charged, or the residues at positions 16, 20, 24 and 28 may all be charged. For example, the residue at position 16 may be Glu or Lys. The residue at position 20 may be Lys. The residue at position 24 may be Glu. The residue at position 28 may be Lys.

Substitution of one or both of the naturally-occurring Gln residues at positions 20 and 24 also reduces the potential for deamidation in acidic solution, thereby increasing the chemical stability of the compounds.

Substitution of one or more of the naturally occurring amino acids at positions 16, 17, 20, 27 and 28 with a charged amino acid enables conjugation to a lipophilic substituent. For example, the residues at positions 16, 17, 20, 27 or 28 may be Cys, Orn or Lys. More particularly, one or more of the residues at positions 16, 17, 20, 27 and 28 may be Cys. Further, one or more of the the residues at positions 16, 17, 20, 27 and 28 may be Lys.

As already disclosed, a compound of the invention may comprise a C-terminal peptide sequence Z of 1-20 amino acids, for example to stabilise the conformation and/or secondary structure of the glucagon analogue peptide, and/or to render the glucagon analogue peptide more resistant to enzymatic hydrolysis, e.g. as described in WO99/46283.

When present, Z represents a peptide sequence of 1-20 amino acid residues, e.g. in the range of 1-15, more preferably in the range of 1-10, in particular in the range of 1-7 amino acid residues, e.g., 1, 2, 3, 4, 5, 6 or 7 amino acid residues, such as 6 amino acid residues. Each of the amino acid residues in the peptide sequence Z may independently be selected from Ala, Leu, Ser, Thr, Tyr, Cys, Glu, Lys, Arg, Dbu (2,4 diaminobutyric acid), Dpr (2,3-diaminopropanoic acid) and Orn (ornithine). Preferably, the amino acid residues are selected from Ser, Thr, Tyr, Glu, Lys, Arg, Dbu, Dpr and Orn, more preferably selected exclusively from Glu, Lys, and Cys. The above-mentioned amino acids may have either D- or L-configuration, but preferably have an L-configuration. Particularly preferred sequences Z are sequences of four, five, six or seven consecutive lysine residues (i.e. $Lys_3$, $Lys_4$, $Lys_5$, $Lys_6$ or $Lys_7$), and particularly five or six consecutive lysine residues. Other exemplary sequences of Z are shown in WO 01/04156. Alternatively the C-terminal residue of the sequence Z may be a Cys residue. This may assist in modification (e.g. PEGylation, or conjugation to albumin) of the compound. In such embodiments, the sequence Z may, for example, be only one amino acid in length (i.e. Z=Cys) or may be two, three, four, five, six or even more amino acids in length. The other amino acids therefore serve as a spacer between the peptide X and the terminal Cys residue.

The peptide sequence Z has no more than 25% sequence identity with the corresponding sequence of the IP-1 portion of human OXM (which has the sequence Lys-Arg-Asn-Arg-Asn-Asn-Ile-Ala) (SEQ ID NO:2).

"Percent (%) amino acid sequence identity" of a given peptide or polypeptide sequence with respect to another polypeptide sequence (e.g. IP-1) is calculated as the percentage of amino acid residues in the given peptide sequence that are identical with correspondingly positioned amino acid residues in the corresponding sequence of that other polypeptide when the two are aligned with one another, introducing gaps for optimal alignment if necessary. % identity values may be determined using WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Thus, when Z is aligned optimally with the 8 amino acids of IP-1, it has no more than two amino acids which are identical with the corresponding amino acids of IP-1.

In a specific embodiment, the present invention provides a compound wherein Z is absent.

One or more of the amino acid side chains in the compound of the invention may be conjugated to a lipophilic substituent. The lipophilic substituent may be covalently bonded to an atom in the amino acid side chain, or alternatively may be conjugated to the amino acid side chain by a spacer. A lipophilic substituent may be conjugated to a side chain of an amino acid which is part of the peptide X, and/or part of the peptide Z.

Without wishing to be bound by any particular theory, it is thought that the lipophilic substituent binds albumin in the blood stream, thus shielding the compounds of the invention from enzymatic degradation and thereby enhancing the half-life of the compounds. The spacer, when present, is used to provide spacing between the compound and the lipophilic substituent.

The lipophilic substituent may be attached to the amino acid side chain or to the spacer via an ester, a sulphonyl ester, a thioester, an amide or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic substituent may include a hydrocarbon chain having 4 to 30 C atoms. Preferably it has at least 8 or 12 C atoms, and preferably it has 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with acyl, and accordingly the hydrocarbon chain may be part of an alkanoyl group, for example palmitoyl, caproyl, lauroyl, myristoyl or stearoyl.

Accordingly, the lipophilic substituent may have the formula shown below:

A may be, for example, an acyl group, a sulphonyl group, NH, N-alkyl, an O atom or an S atom, preferably acyl. n is an integer from 3 to 29, preferably at least 7 or at least 11, and preferably 23 or less, more preferably 19 or less.

The hydrocarbon chain may be further substituted. For example, it may be further substituted with up to three substituents selected from $NH_2$, OH and COOH. If the hydrocarbon chain is further substituted, preferably it is further substituted with only one substituent. Alternatively or additionally, the hydrocarbon chain may include a cycloalkane or heterocycloalkane, for example as shown below:

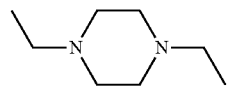

Preferably the cycloalkane or heterocycloalkane is a six-membered ring. Most preferably, it is piperidine.

Alternatively, the lipophilic substituent may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As mentioned above, the lipophilic substituent may be conjugated to the amino acid side chain by a spacer. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may have the formula:

wherein B and D are each independently selected from acyl, sulphonyl, NH, N-alkyl, an O atom and an S atom, preferably from acyl and NH. Preferably, n is an integer from 1 to 10, preferably from 1 to 5. The spacer may be further substituted with one or more substituents selected from $C_{0-6}$ alkyl, $C_{0-6}$ alkyl amine, $C_{0-6}$ alkyl hydroxy and $C_{0-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic substituent as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalised side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gln, Asn, α-Glu, γ-Glu, Asp, Ser Thr, Gaba, Aib, β-Ala, 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from γ-Glu, Gaba, β-Ala and α-Glu.

A lipophilic substituent may be conjugated to any amino acid side chain in a compound of the invention. Preferably, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. Preferably, the lipophilic substituent is conjugated to Lys. An amino acid shown as Lys in the formulae provided herein may be replaced by, e.g., Dbu, Dpr or Orn where a lipophilic substituent is added.

An example of a lipophilic substituent and spacer is shown in the formula below:

ability. Such modification is also known to reduce clearance (e.g. renal clearance) of therapeutic proteins and peptides.

The polymeric moiety is preferably water-soluble (amphiphilic or hydrophilic), non-toxic, and pharmaceutically inert. Suitable polymeric moieties include polyethylene glycol (PEG), homo- or co-polymers of PEG, a monomethyl-substituted polymer of PEG (mPEG), and polyoxyethylene glycerol (POG). See, for example, *Int. J. Hematology* 68:1 (1998); *Bioconjugate Chem.* 6:150 (1995); and *Crit. Rev. Therap. Drug Carrier Sys.* 9:249 (1992).

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57; Tsukada, et al. (1984), J. Natl. Cancer Inst., vol 73, 721-729; and Pratesi, et al. (1985), Br. J. Cancer, vol. 52: 841-848).

The polymeric moiety may be straight-chain or branched. It may have a molecular weight of 500-40,000 Da, for example 500-10,000 Da, 1000-5000 Da, 10,000-20,000 Da, or 20,000-40,000 Da.

A compound of the invention may comprise two or more such moieties, in which case the total molecular weight of all such moieties will generally fall within the ranges provided above.

The polymeric moiety may be coupled (by covalent linkage) to an amino, carboxyl or thiol group of an amino acid side chain. Preferred examples are the thiol group of Cys residues and the epsilon amino group of Lys residues. The carboxyl groups of Asp and Glu residues may also be used.

The skilled reader will be well aware of suitable techniques that can be used to perform the coupling reaction. For example, a PEG moiety carrying a methoxy group can be coupled to a Cys thiol group by a maleimido linkage using reagents commercially available from Nektar Therapeutics AL. See also WO 2008/101017, and the references cited above, for details of suitable chemistry.

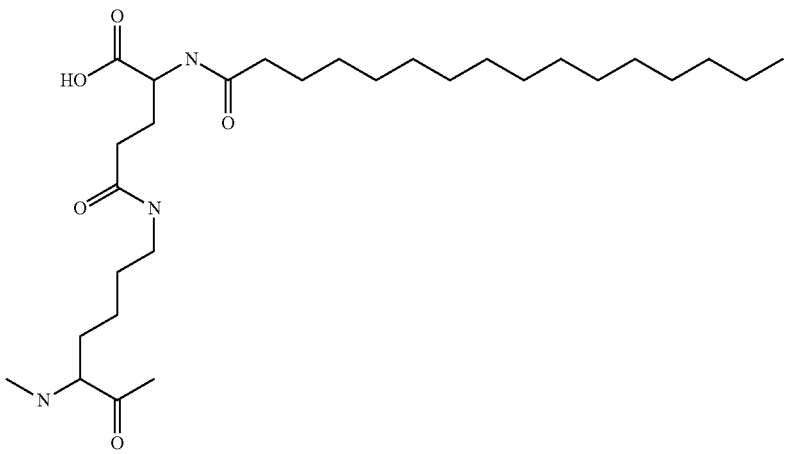 [SMILES: CCCCCCCCCCCCCCCC(=O)NC(CCC(=O)NCCCCC(NC)C(C)=O)C(=O)O]

Here, a Lys residue in the compound of the present invention is covalently attached to γ-Glu (the spacer) via an amide moiety. Palmitoyl is covalently attached to the γ-Glu spacer via an amide moiety.

Alternatively or additionally, one or more amino acid side chains in the compound of the invention may be conjugated to a polymeric moiety, for example, in order to increase solubility and/or half-life in vivo (e.g. in plasma) and/or bioavail- In another aspect, one or more of the amino acid side chains in a compound in the present invention, for example in peptide X, is/are conjugated to a polymeric moiety.

In a further aspect, the present invention provides a composition comprising a compound of the invention as described herein, or a salt or derivative thereof, in admixture with a carrier.

The term "derivative thereof" refers to a derivative of any one of the compounds. Derivatives include all chemical modifications, all conservative variants, all prodrugs and all metabolites of the compounds.

The invention also provides the use of a compound of the present invention in the preparation of a medicament for the treatment of a condition as described below.

The invention also provides a composition wherein the composition is a pharmaceutically acceptable composition, and the carrier is a pharmaceutically acceptable carrier.

Peptide Synthesis

The compounds of the present invention may be manufactured either by standard synthetic methods, recombinant expression systems, or any other state of the art method. Thus the glucagon analogues may be synthesized in a number of ways, including, for example, a method which comprises:

(a) synthesizing the peptide by means of solid-phase or liquid-phase methodology, either stepwise or by fragment assembly, and isolation and purifying of the final peptide product; or (b) expressing a nucleic acid construct that encodes the peptide in a host cell, and recovering the expression product from the host cell culture; or (c) effecting cell-free in vitro expression of a nucleic acid construct that encodes the peptide, and recovering the expression product;

or any combination of methods of (a), (b), and (c) to obtain fragments of the peptide, subsequently ligating the fragments to obtain the peptide, and recovering the peptide.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments of the invention will normally be inserted in suitable vectors to form cloning or expression vectors carrying the nucleic acid fragments of the invention; such novel vectors are also part of the invention. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the compound of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment are useful embodiments of the invention; they can be used for small-scale or large-scale preparation of the peptides of the invention.

When producing the peptide of the invention by means of transformed cells, it is convenient, although far from essential, that the expression product is secreted into the culture medium.

Efficacy

Binding of the relevant compounds to GLP-1 or glucagon (Glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may employ the human glucagon receptor (Glucagon-R) having primary accession number GI:4503947 and/or the human glucagon-like peptide 1 receptor (GLP-1R) having primary accession number GI:166795283. (in that where sequences of precursor proteins are referred to, it should of course be understood that assays may make use of the mature protein, lacking the signal sequence).

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$[GLP-1] lower than the $EC_{50}$ [GLP-1] of glucagon in a particular assay may be considered to have higher GLP-1 receptor agonist potency than glucagon.

The compounds described in this specification are typically Glu-GLP-1 dual agonists, as determined by the observation that they are capable of stimulating cAMP formation at both the glucagon receptor and the GLP-1 receptor. The stimulation of each receptor can be measured in independent assays and afterwards compared to each other.

By comparing the $EC_{50}$ value for the glucagon receptor ($EC_{50}$[Glucagon-R]) with the $EC_{50}$ value for the GLP-1 receptor, ($EC_{50}$ [GLP-1R]) for a given compound, the relative glucagon selectivity (%) of that compound can be found as follows:

Relative Glucagon-$R$ selectivity[compound]=(1/$EC_{50}$ [Glucagon-$R$])×100/(1/$EC_{50}$[Glucagon-$R$]+1/ $EC_{50}$[GLP-1$R$])

The relative GLP-1R selectivity can likewise be found:

Relative GLP-1$R$ selectivity[compound]=(1/$EC_{50}$ [GLP-1$R$])×100/(1/$EC_{50}$[Glucagon-$R$]+1/$EC_{50}$ [GLP-1$R$])

A compound's relative selectivity allows its effect on the GLP-1 or glucagon receptor to be compared directly to its effect on the other receptor. For example, the higher a compound's relative GLP-1 selectivity is, the more effective that compound is on the GLP-1 receptor as compared to the glucagon receptor.

Using the assays described below, we have found the relative GLP-1 selectivity for human glucagon to be approximately 5%.

The compounds of the invention have a higher relative GLP-1R selectivity than human glucagon in that for a particular level of glucagon-R agonist activity, the compound will display a higher level of GLP-1R agonist activity (i.e. greater potency at the GLP-1 receptor) than glucagon. It will be understood that the absolute potency of a particular compound at the glucagon and GLP-1 receptors may be higher, lower or approximately equal to that of native human glucagon, as long as the appropriate relative GLP-1R selectivity is achieved.

Nevertheless, the compounds of this invention may have a lower $EC_{50}$ [GLP-1R] than human glucagon. The compounds may have a lower $EC_{50}$ [GLP-1-R] than glucagon while maintaining an $EC_{50}$ [Glucagon-R] that is less than 10-fold higher than that of human glucagon, less than 5-fold higher than that of human glucagon, or less than 2-fold higher than that of human glucagon.

The compounds of the invention may have an $EC_{50}$ [Glucagon-R] that is less than two-fold that of human glucagon. The compounds may have an $EC_{50}$ [Glucagon-R] that is less than two-fold that of human glucagon and have an $EC_{50}$ [GLP-1R] that is less than half that of human glucagon, less than a fifth of that of human glucagon, or less than a tenth of that of human glucagon.

The relative GLP-1R selectivity of the compounds may be between 5% and 95%. For example, the compounds may have a relative selectivity of 5-20%, 10-30%, 20-50%, 30-70%, or 50-80%; or of 30-50%, 40-60,%, 50-70% or 75-95%.

The compounds of the invention may also have effect on other Class B GPCR receptors, such as, but not limited to, Calcitonin gene-related peptide 1 (CGRP1), corticotropin-releasing factor 1 & 2 (CRF1 & CRF2), gastric inhibitory polypeptide (GIP), glucagon-like peptide 1 & 2 (GLP-1 & GLP-2, glucagon (GCGR), secretin, gonadotropin releasing hormone (GnRH), parathyroid-hormone 1 & 2 (PTH1 & PTH2), vasoactive intestinal peptide (VPAC1 & VPAC2).

Therapeutic Uses

The compounds of the invention may provide an attractive treatment option for, inter alia, obesity and metabolic diseases.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with the metabolic syndrome are at increased risk of coronary heart disease and other diseases related to other manifestations of arteriosclerosis (e.g., stroke and peripheral vascular disease). The dominant underlying risk factors for this syndrome appear to be abdominal obesity.

Without wishing to be bound by any particular theory, it is believed that the compounds of the invention act as GluGLP-1 dual agonists. The dual agonist combines the effect of glucagon on fat metabolism with the effects of GLP-1 on food intake. They might therefore act in a synergistic fashion to accelerate elimination of excessive fat deposition and induce sustainable weight loss.

The synergistic effect of dual GluGLP-1 agonists may also result in reduction of cardiovascular risk factors such as high cholesterol and LDL, which may be entirely independent of their effect on body weight.

The compounds of the present invention may therefore be used as pharmaceutical agents for preventing weight gain, promoting weight loss, reducing excess body weight or treating obesity (e.g. by control of appetite, feeding, food intake, calorie intake, and/or energy expenditure), including morbid obesity, as well as associated diseases and health conditions including but not limited to obesity linked inflammation, obesity linked gallbladder disease and obesity induced sleep apnea. The compounds of the invention may also be used for treatment of metabolic syndrome, hypertension, atherogenic dyslipidimia, atherosclerois, arteriosclerosis, coronary heart disease and stroke. These are all conditions which can be associated with obesity. However, the effects of the compounds of the invention on these conditions may be mediated in whole or in part via an effect on body weight, or may be independent thereof.

In particular, the compounds described in the present invention may find use in preventing weight gain or promoting weight loss with no or little effect on glucose tolerance. It has been found that the compounds described has marked effect on weight loss with no or little effect on the HbA1c level in an suitable glycemic control animal model.

Thus the invention provides use of a compound of the invention in the treatment of a condition as described above, in an individual in need thereof.

The invention also provides a compound of the invention for use in a method of medical treatment, particularly for use in a method of treatment of a condition as described above.

In a preferred aspect, the compounds described may be used in preventing weight gain or promoting weight loss.

In a specific embodiment, the present invention comprises use of a compound for preventing weight gain or promoting weight loss in an individual in need thereof.

In a specific embodiment, the present invention comprises use of a compound in a method of treatment of a condition caused or characterised by excess body weight, e.g. the treatment and/or prevention of obesity, morbid obesity, morbid obesity prior to surgery, obesity linked inflammation, obesity linked gallbladder disease, obesity induced sleep apnea, hypertension, atherogenic dyslipidimia, atherosclerois, arteriosclerosis, coronary heart disease, peripheral artery disease, stroke or microvascular disease in an individual in need thereof.

In another aspect, the compounds described may be used in a method of lowering circulating LDL levels, and/or increasing HDL/LDL ratio.

In a specific embodiment, the present invention comprises use of a compound in a method of lowering circulating LDL levels, and/or increasing HDL/LDL ratio in an individual in need thereof.

Pharmaceutical Compositions

The compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompases any agents listed in the US Pharmacopeia for use in animals, including humans.

The term "pharmaceutically acceptable salt" refers to a salt of any one of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

Subcutaneous or transdermal modes of administration may be particularly suitable for the compounds described herein.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Combination Therapy

As noted above, it will be understood that reference in the following to a compound of the invention also extends to a pharmaceutically acceptable salt or solvate thereof as well as to a composition comprising more than one different compounds of the invention.

A compound of the invention may be administered as part of a combination therapy with an agent for treatment of obesity, hypertension dyslipidemia or diabetes.

In such cases, the two active agents may be given together or separately, and as part of the same pharmaceutical formulation or as separate formulations.

Thus a compound or salt thereof can further be used in combination with an anti-obesity agent, including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

A compound of the invention or salt thereof can be used in combination with an anti-hypertension agent, including but not limited to an angiotensin-converting enzyme inhibitor, angiotensin II receptor blocker, diuretics, beta-blocker, or calcium channel blocker.

A compound of the invention or salt thereof can be used in combination with a dyslipidaemia agent, including but not limited to a statin, a fibrate, a niacin and/or a cholesterol absorbtion inhibitor.

Further, a compound of the invention or salt thereof can be used in combination with an anti-diabetic agent, including but not limited to metformin, a sulfonylurea, a glinide, a DPP-IV inhibitor, a glitazone, a different GLP-1 agonist or an insulin. In a preferred embodiment, the compound or salt thereof is used in combination with insulin, DPP-IV inhibitor, sulfonylurea or metformin, particularly sulfonylurea or metformin, for achieving adequate glycemic control. In an even more preferred embodiment the compound or salt thereof is used in combination with an insulin or an insulin analogue for achieving adequate glycemic control. Examples of insulin analogues include but are not limited to LANTUS®, NOVORAPID®, HUMALOG®, NOVOMIX®, and Actraphane HM.

Methods

General Synthesis of Glucagon Analogues

Solid phase peptide synthesis (SPPS) was performed on a microwave assisted synthesizer using standard Fmoc strategy in NMP on a polystyrene resin (TENTAGEL® S Ram). HATU was used as coupling reagent together with DIPEA as base. Piperidine (20% in NMP) was used for deprotection. Pseudoprolines: Fmoc-Phe-Thr(.Psi. Me, Me pro)-OH and Fmoc-Asp-Ser(.Psi., Me, Me pro)-OH (purchased from NOVABIOCHEM®) were used where applicable.

Abbreviations employed are as follows:
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
$Et_2O$: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane Cleavage:

The crude peptide was cleaved from the resin by treatment with 95/2.5/2.5% (v/v) TFA/TIS/water at r.t. for 2 h. For peptides with a methionine in the sequence a mixture of 95/5% (v/v) TFA/EDT was used. Most of the TFA was removed at reduced pressure and the crude peptide was precipitated and washed with diethylether and allowed to dry to constant weight at ambient temperature.

General Synthesis of Acylated Glucagon Analogues

The peptide backbone was synthesized as described above for the general synthesis of glucagon analogues, with the exception that it was acylated on the side chain of a lysine residue with the peptide still attached to the resin and fully protected on the side chain groups, except the epsilon-amine on the lysine to be acylated. The lysine to be acylated was incorporated with the use of Fmoc-Lys(ivDde)-OH or Fmoc-Lys(Dde)-OH. The N-terminal of the peptide was protected with a Boc group using $Boc_2O$ in NMP. While the peptide was still attached to the resin, the ivDde protecting group was selectively cleaved using 5% hydrazine hydrate in NMP. The unprotected lysine side chain was then first coupled with a spacer amino acid like Fmoc-Glu-OtBu, which was deprotected with piperidine and acylated with a fatty acid using standard peptide coupling methodology as described above. Alternatively, the histidine at the N-terminal may be incorporated from the beginning as Boc-His(Boc)-OH. Cleavage from the resin and purification were performed as described above.

Generation of Cell Lines Expressing Human Glucagon- and GLP-1 Receptors

The cDNA encoding either the human glucagon receptor (Glucagon-R) (primary accession number P47871) or the human glucagon-like peptide 1 receptor (GLP-1R) (primary accession number P43220) were cloned from the cDNA clones BC104854 (MGC:132514/IMAGE:8143857) or BC112126 (MGC:138331/IMAGE:8327594), respectively. The DNA encoding the Glucagon-R or the GLP-1-R was amplified by PCR using primers encoding terminal restriction sites for subcloning. The 5'-end primers additionally encoded a near Kozak consensus sequence to ensure efficient translation. The fidelity of the DNA encoding the Glucagon-R and the GLP-1-R was confirmed by DNA sequencing. The PCR products encoding the Glucagon-R or the GLP-1-R were subcloned into a mammalian expression vector containing a neomycin (G418) resistance marker. The mammalian expression vectors encoding the Glucagon-R or the GLP-1-R were transfected into HEK293 cells by a standard calcium phosphate transfection method. 48 hr after transfection cells were seeded for limited dilution cloning and selected with 1 mg/ml G418 in the culture medium. Three weeks later 12 surviving colonies of Glucagon-R and GLP-1-R expressing cells were picked, propagated and tested in the Glucagon-R and GLP-1-R efficacy assays as described below. One Glucagon-R expressing clone and one GLP-1-R expressing clone were chosen for compound profiling.

Glucagon Receptor and GLP-1-Receptor Efficacy Assays

HEK293 cells expressing the human Glucagon-R, or human GLP-1-R were seeded at 40,000 cells per well in 96-well microtiter plates coated with 0.01% poly-L-lysine and grown for 1 day in culture in 100 µl growth medium. On the day of analysis, growth medium was removed and the cells washed once with 200 µl Tyrode buffer. Cells were incubated in 100 µl Tyrode buffer containing increasing concentrations of test peptides, 100 µM IBMX, and 6 mM glucose for up 15 min at 37° C. The reaction was stopped by addition of 25 µl 0.5 M HCl and incubated on ice for 60 min. The cAMP content was estimated using the Flash Plate® cAMP kit from Perkin-Elmer according to manufacturer instructions. $EC_{50}$ and relative efficacies compared to reference compounds (glucagon and GLP-1) were estimated by computer aided curve fitting.

HbA1c Determination

It is possible to assess the long term effect of a compound on a subject's glucose level by determining the level of haemoglobin A1C (HbA1c). HbA1c is a glycosylated form of haemoglobin whose level in a cell reflects the average level of glucose to which the cell has been exposed during its lifetime. In mice, HbA1c is a relevant biomarker for the average blood glucose level during the preceding 4 weeks, because conversion to HbA1c is limited by the erythrocyte's life span of approximately 47 days (Abbrecht & Littell, 1972; J. Appl. Physiol. 32, 443-445).

The HbA1c determination is based on Turbidimetric INhibition ImmunoAssay (TINIA) in which HbA1c in the sample reacts with anti-HbA1c to form soluble antigen-antibody complexes. Additions of polyhaptens react with excess anti-HbA1c antibodies to form an insoluble antibody-polyhapten complex, which can be measured turbidimetrically. Liberated hemoglobin in the hemolyzed sample is converted to a derivative having a characteristic absorption spectrum, which is measured bichromatically during the preincubation phases. The final result is expressed as percent HbA1c of total hemoglobin (Cobas®Application note A1C-2).

Cholesterol Level Determination

The assay is an enzymatic colorimetric method. In the presence of magnesium ions, dextran sulfate selectively forms water-soluble complexes with LDL, VLDLA and chylomicrons, which are resistant to PEG-modified enzymes. The HDL cholesterol is determined enzymatically by cholesterol esterase and cholesterol oxidase coupled with PEG to the amino groups. Cholesterol esters are broken down quantitatively to free cholesterol and fatty acids. HDL cholesterol is enzymatically oxidized to choles-4-en-3-one and $H_2O_2$, and the formed $H_2O_2$ is measured colorimetrically (Cobas®; Application note HDLC3).

The direct determination of LDL takes advantage of the selective micellary solubilization of LDL by a nonionic detergent and the interaction of a sugar compound and lipoproteins (VLDL and chylomicrons). The combination of a sugar compound with detergent enables the selective determination of LDL in plasma. The test principle is the same as that of cholesterol and HDL, but due to the sugar and detergent only LDL-cholesterol esters are broken down to free cholesterol and fatty acids. Free cholesterol is then oxidized and the formed $H_2O_2$ is measured colorimetrically (Application note LDL_C, Cobas®).

Tested GPCR-B Targets

Receptors for: Calcitonin gene-related peptide 1 (CGRP1), corticotropin-releasing factor 1 & 2 (CRF1 & CRF2), gastric inhibitory polypeptide (GIP), glucagon-like peptide 1 & 2 (GLP-1 & GLP-2, glucagon (GCGR), secretin, gonadotropin releasing hormone (GnRH), parathyroid-hormone 1 & 2 (PTH1 & PTH2), vasoactive intestinal peptide (VPAC1 & VPAC2).

Assay Design for Other Class B Receptors

Agonist percentage activation determinations were obtained by assaying sample compounds (glucagon analogues) and referencing the Emax control for each GPCR profiled. Antagonist percentage inhibition determinations were obtained by assaying sample compounds and referencing the control EC80 wells for each GPCR profiled. The samples were run using a "Double Addition" assay protocol for the agonist and antagonist assay run. The protocol design is as follows:

Compound Preparation Master Stock Solution

Unless specified otherwise, the sample compounds were diluted in 100% anhydrous DMSO including all dilutions. If the sample compound is provided in a different solvent all master stock dilutions are performed in the specified solvent. All control wells contained identical solvent final concentrations as the sample compound wells.

Compound Plate for Assay

The glucagon analogues were transferred from a master stock solution into a daughter plate that was used in the assay. Each sample compound was diluted into assay buffer (1×HBSS with 20 mM HEPES and 2.5 mM Probenecid) at an appropriate concentration to obtain final specified concentrations.

Calcium Flux Assay Agonist Assay Format

The glucagon analogues were plated in duplicate at 100 nM and 1 nM. The concentrations described here reflect the final concentrations of the compounds during the antagonist assay. Reference agonists were handled as mentioned above serving as assay control. The reference agonists were handled as described above for Emax. Assay was read for 90 seconds using the FLIPR$^{TETRA}$ Antagonist Assay Format Using the EC80 values determined previously, stimulated all pre-incubated sample compound and reference antagonist (if applicable) wells with $EC_{80}$ of reference agonist.

Read for 180 seconds using the FLIPR$^{TETRA}$ (this addition added reference agonist to respective wells)—then fluorescence measurements were collected to calculate $IC_{50}$-values.

PK in Cynomolgus Monkeys

Cynomolgus monkeys (male, N=2) were dosed with 20 nmol compound 6/kg i.v. and 20 nmol compound 6/kg s.c. as single dose at day 1 and 8, respectively. Plasma samples were withdrawn at the following time points; predose, 5, 10, 30 min, 1, 2, 4, 8, 12, 24 and 36 h post i.v. dosing and predose, 10, 30 min, 1, 2, 4, 8, 12, 24, 36 and 48 h post s.c. dosing. The vehicle consisted of 25 mM phosphate buffered saline at pH 7.4 (25 mM sodium phosphate, 25 mM NaCl). Plasma samples were analyzed using protein precipitation followed by solid phase extraction and LC-MS/MS analysis. Pharmacokinetic parameters were calculated using non-compartmental analysis in WinNonLin version 4.1.

Effect of 6 Weeks Subcutaneous Administration of Glu-GLP-1 Agonist Compound 6 on HbA1c in db/db Mice db/db (BKS.Cg-m+/+ Lepr$^{db}$/J) male mice, 5-6 weeks old, were obtained from Charles River Laboratories, Germany, and acclimatized in their new environment with free access to normal chow and water. The animals were stratified into groups with similar average HbA1c and treated twice daily s.c. with compound 6 (1, 2.5, and 5 nmol/kg) or vehicle for six weeks. Throughout the study, body weights were recorded daily and used to administer the body weight-corrected doses of peptide. HbA1c levels were measured on blood samples before treatment, and then once weekly during the study. Immediately following final blood sampling, all animals were sacrificed.

Effect of Three Weeks Treatment with the Dual Glu-GLP-1 Agonist Compound 6 on Oral Glucose Tolerance and Body Weight in Diet Induced Obese Mice (30 Weeks High-Fat Diet).

C57Bl/6J male mice, 6 weeks old, were acclimatized in their new environment with free access to a high fat diet and water. 36 weeks old, the animals were randomized into groups with similar average fasting (6 hours) blood glucose (assessed from blood samples taken from the tip of the tail). The mice were treated twice daily s.c. for three weeks with compound 6 or vehicle. Body weight was recorded daily. After peptide treatment an oral glucose tolerance test (OGTT) were performed after subjecting the animals to a 6 hour fast. Animals were dosed with peptide or vehicle in the morning. Approximately four hours later an initial blood sample (fasting blood glucose level) was taken. Thereafter an oral dose of glucose was given and the animals were returned to their home cages (t=0). BG was measured at t=15 min, t=30 min, t=60 min, t=90 min and t=120 min. All animals were sacrificed immediately following blood sampling by $CO_2$ anesthesia followed by cervical dislocation.

The invention is further illustrated by the following examples.

Example 1

Efficacy on Glucagon and GLP-1 Receptors

TABLE 1

$EC_{50}$ values were measured as described above

| Compound No | SEQ ID No | Sequence | GLP-1R $EC_{50}$ (nM) | GluR $EC_{50}$ (nM) |
|---|---|---|---|---|
| 1 | 4 | H-HSQGTFTSDYSKYLDERRAKDFIEWLLSA-NH2 | 0.06 | 0.06 |
| 2 | 5 | H-HSQGTFTSDYSKYLDERRAKDFIEWL-K(Hexadecanoyl-isoGlu)-SA-NH2 | 3.09 | 0.81 |
| 3 | 6 | H-HSQGTFTSDYSKYLDERRA-K(Hexadecanoyl-isoGlu)-DFIEWLLSA-NH2 | 0.64 | 0.60 |
| 4 | 7 | H-HSQGTFTSDYSKYLDERRAKDFIEWLL-K(Hexadecanoyl-isoGlu)-A-NH2 | 0.31 | 0.25 |
| 5 | 8 | H-HSQGTFTSDYSKYLD-K(Hexadecanoyl-isoGlu)-RRAKDFIEWLLSA-NH2 | 0.35 | 0.19 |
| 6 | 9 | H-HSQGTFTSDYSKYLDE-K(Hexadecanoyl-isoGlu)-RAKDFIEWLLSA-NH2 | 0.13 | 0.16 |
| 7 | 10 | H-H-Aib-QGTFTSDYSKYLDE-K(Hexadecanoyl-isoGlu)-RAKDFIEWLLSA-NH2 | 0.10 | 0.16 |

Example 2

Pharmacokinetic Study Following Subcutaneous and Intravenous Administration in the Monkey Compound 6 was dosed to monkeys in order to test the pharmacokinetics and bioavailability after subcutaneous administration, which is the intended route in humans. Compound 6 showed a bioavailability of 43%±8.1, $t_{1/2}$ of 8.2 h±2.0 and $t_{max}$ between 4 and 8 h. The pharmacokinetic profile, of compound 6 is likely to predict constant exposure above $EC_{50}$ at both the glucagon and GLP-1 receptors in humans after once daily administration of a feasible dose by the subcutaneous route.

Example 3

Effect of 6 Weeks Subcutaneous Administration of Glu-GLP-1 Agonist Compound 6 on HbA1c in db/db Mice The animals were injected s.c. with 100 μl vehicle (once a day) for a period of three days to acclimatize the animals to handling and injections. The animals were randomized into groups with similar average HbA1c. Then mice were treated twice daily s.c. with compound 6 (1, 2.5, or 5 nmol/kg) or vehicle. Before treatment and once weekly for six weeks of treatment, blood samples were taken from the retroorbital venous plexus.

Blood samples were analyzed for HbA1c using the Cobas c111 analyzer (Roche Diagnostics, Mannheim, Germany). Samples for HbA1c analysis were analyzed within 24 hours of sampling.

Throughout the study, body weights were recorded daily and used to administer the body weight-corrected doses of peptide. Solutions were prepared immediately before dosing.

As expected from the db/db mouse model an increase in HbA1c over time was seen (FIG. 1). During the six weeks treatment we observed a 27% increase in HbA1c in the vehicle group.

Compound 6, at all doses, did not at any time-point reduce the increase in HbA1c seen over time in vehicle-treated animals (FIG. 1).

Figure 2:
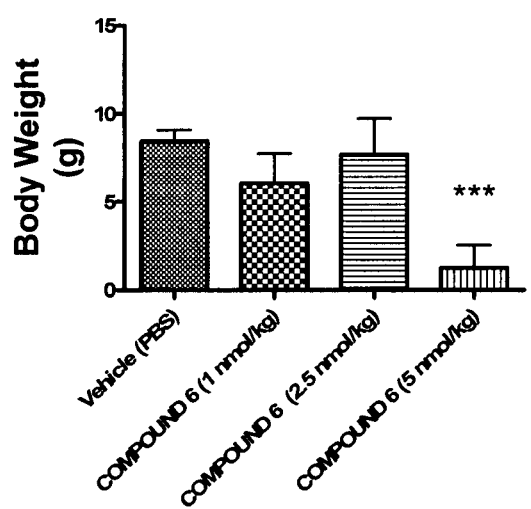
FIG. 2: Effect of s.c. administration of the Glu-GLP-1 agonist compound 6 on body weight gain over the 6 weeks treatment period in db/db mice. Data are given as mean+SEM with n=11/group. p<0.01, *p<0.001 compared to vehicle.

During the six weeks treatment we observed a 22% increase in body weight in the vehicle group. Compound 6 (5 nmol/kg) significantly decreased body weight gain compared to vehicle (p<0.0001, FIG. 2).

The effect of six weeks treatment with the dual Glu-GLP-1 agonist compound 6 on glycemic control as assessed by HbA1c in db/db mice was investigated.

The db/db mouse model, as expected, showed an increase in HbA1c over time. Treatment with compound 6 for six weeks did not significantly reduce the increase in HbA1c seen over time in vehicle-treated db/db mice.

Treatment with compound 6 (5 nmol/kg) for six weeks significantly reduced the increase in body weight seen over time in vehicle-treated db/db mice.

Example 4

Effect of 3 Weeks Subcutaneous Administration of Glu-GLP-1 Agonist Compound 6 on Oral Glucose Tolerance and Body Weight in Diet Induced Obese C57BL/6J Mice (6 Months High Fat Diet)

Body Weight

Figure 3:
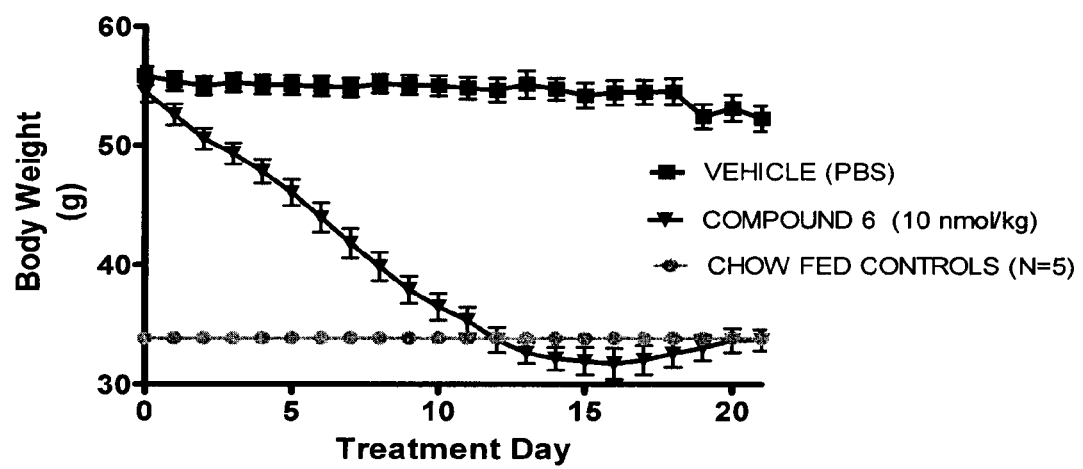
FIG. 3: Effect of s.c. administration the Glu-GLP-1 agonist compound 6 on body weight in high fat fed C57BL/6J mice. Data are mean±SEM.

Compound 6 decreased the body weight 38.7% (p<0.05) (FIG. 3). Interestingly, the body weight obtained by high fat fed animals treated with compound 6 for three weeks stabilized to the same body weight as obtained by non-treated control animals on a regular chow diet (FIG. 3).

OGTT (Oral Glucose Tolerance Test)

Figure 4:
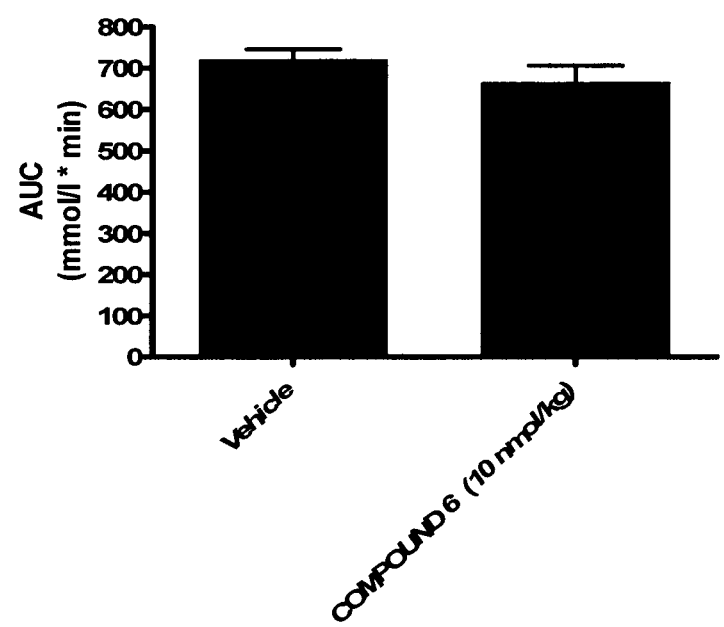
FIG. 4: Effect of s.c. administration of the Glu-GLP-1 agonist compound 6 on area under the glucose curve (AUC) during OGTT in high fat fed C57BL/6J mice. Data are mean+SEM. *p<0.05.

Treatment with compound 6 for three weeks had no significant effect on glucose tolerance (measured as decrease in AUC) (FIG. 4).

Compound 6 significantly decreased body weight in diet induced obese mice (30 weeks high fat diet) to a level as that seen in non-treated control animals on a regular chow diet (FIG. 3). The effect of Compound 6 significantly decreased fasting blood glucose. Compound 6 did not significantly increase oral glucose tolerance.

These differences in weight loss and glucose handling could reflect the potency (Table 1) and/or the exposure on the GLP-1 receptor of the Glu-GLP-1 agonist compound 6. The difference could also be related to differences between GLP-1 and GLP-1 analogs and Glu-GLP-1 agonists in mechanism of action. Exendin-4 and other GLP-1 analogs are known to regulate blood glucose via stimulation of glucose-dependent insulin secretion, inhibition of gastric emptying, and inhibition of glucagon secretion. In addition to effects such as these on the GLP-1 receptor, compound 6 also binds and activates the GluR (see Table 1).

In diet induced obese mice, compound 6 significantly decreased body weight. Compound 6 did not improve glucose tolerance measured during and oral glucose tolerance test.

Example 5

Figure 5:
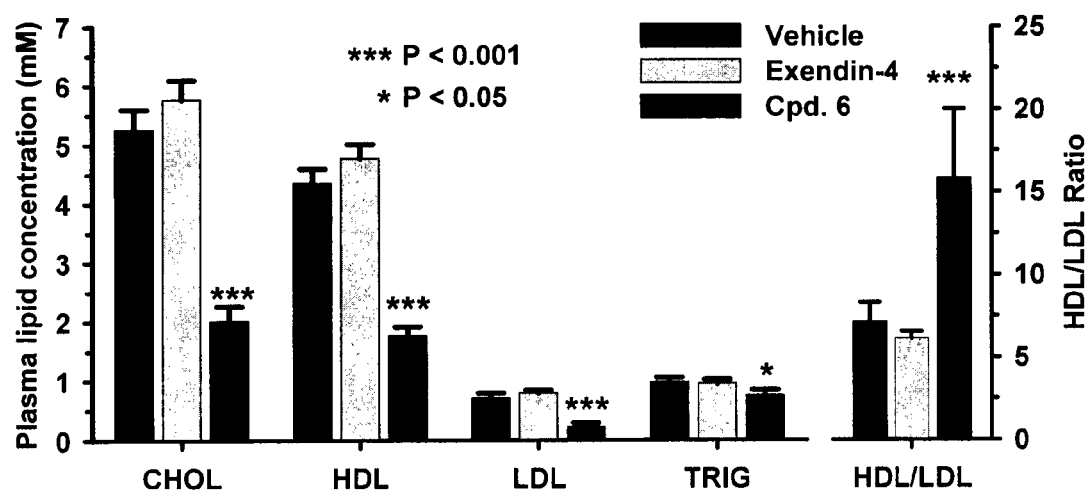
FIG. 5: Effect of 3 weeks treatment of mice that have been on 30 weeks High Fat Diet for 30 weeks prior treatment (s.c.) with vehicle (PBS), 10 nmol/kg exendin-4 or 10 nmol/kg compound 6 twice daily for 3 weeks on lipids. CHO: Total Cholesterol; HDL: High Density Cholesterol; LDL: Low Density Cholesterol; TRIG: Triglycerides; HDL/LDL: Ratio between HDL and LDL.

Effect of 3 Weeks Subcutaneous Administration of Glu-GLP-1 Agonist Compound 6 on Lipids in 30 Weeks High Fat Diet Feeded Mice Effect of 3 weeks treatment of mice that have been on a High Fat Diet for 30 weeks prior to treatment (s.c.) with vehicle (PBS), 10 nmol/kg exendin-4 or 10 nmol/kg compound 6 twice daily for 3 weeks on lipids (FIG. 5). The effect was measured on LDL, HDL and triglycerides (CHO: Total Cholesterol; HDL: High Density Cholesterol; LDL: Low Density Cholesterol; TRIG: Triglycerides; HDULDL: Ratio between HDL and LDL).

Compound 6 demonstrated significantly decreased total cholesterol, HDL, LDL (P<0.001) and triglycerides (P<0.05), while the ratio HDULDL was increased significantly (p<0.001) (FIG. 5). The HDL/LDL ratio is considered to be a risk indicator for heart disease. The higher the ratio, the lower the risk of heart attack or other cardiovascular problems.

Example 6

Counterscreen of Compound 6 Against CGRP and Other Receptors

Compound 6 was tested for agonist and antagonist activity against Calcitonin gene-related peptide 1 (CGRP1), corticotropin-releasing factor 1 & 2 (CRF1 & CRF2), gastric inhibitory polypeptide (GIP), glucagon-like peptide 1 & 2 (GLP-1 & GLP-2, glucagon (GCGR), secretin, gonadotropin releasing hormone (GnRH), parathyroid-hormone 1 & 2 (PTH1 & PTH2), vasoactive intestinal peptide (VPAC1 & VPAC2) at 1 (1.25), 100 (125) and 10,000 (12,500) nM.

Agonist activity against the following receptors was observed:
GLP-1 receptor: compound 6 exhibited agonist activities at 12.5 µM and 125 nM
Glucagon receptor compound 6 exhibited agonist activities at 12.5 µM and 125 nM
Antagonist activity against the following receptors was observed:
CRF2 receptor. Compound 6 exhibited antagonist activity at 10 µM
GIP receptor: Compound 6 exhibited antagonist activity at 10 µM and 100 nM
Secretin receptor: Compound 6 exhibited antagonist activity at 10 µM.

Example 7

Figure 6:
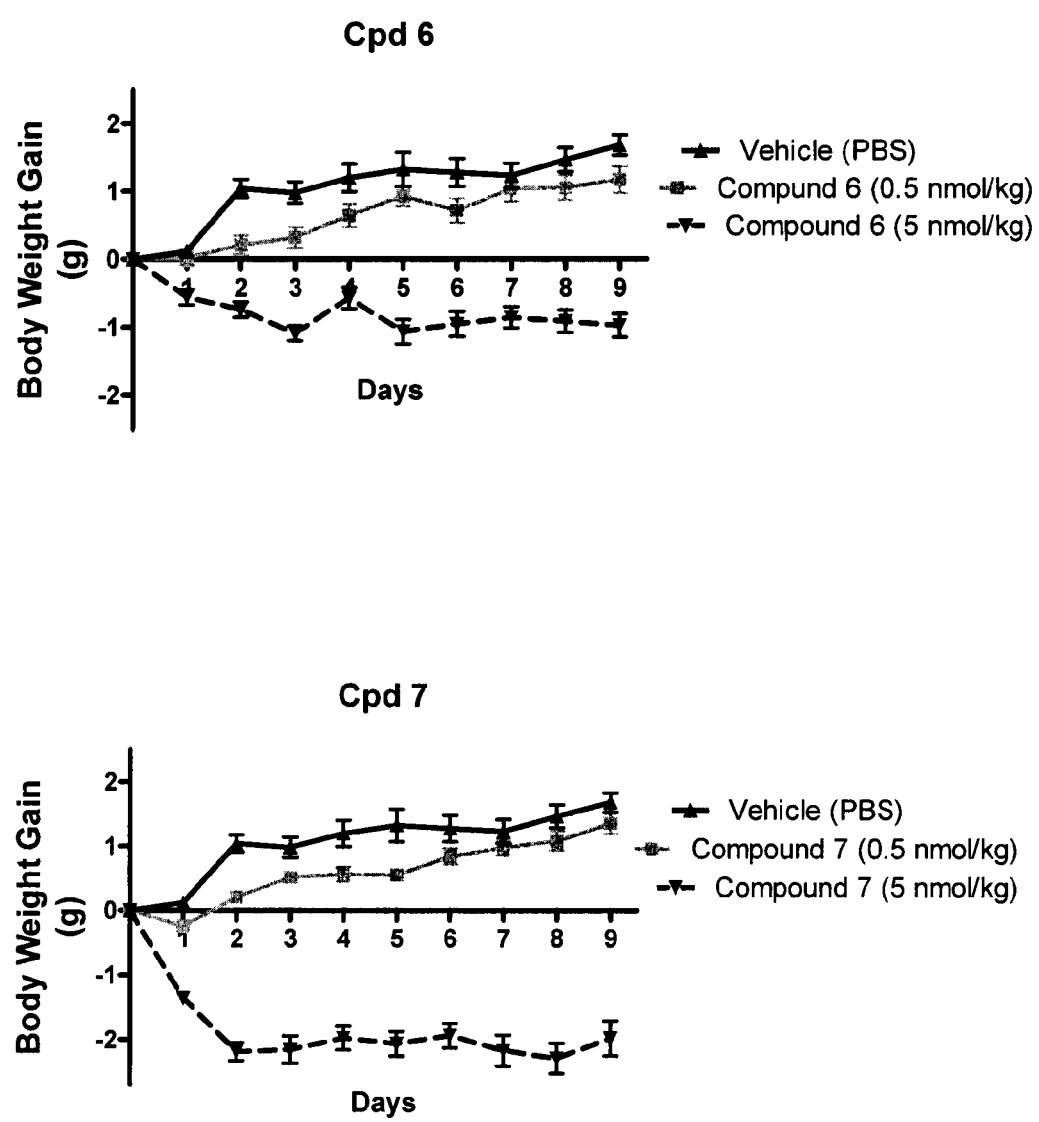
FIG. 6: The effect of compound 6 and compound 7 on body weight gain in high fat fed C57BL/6J mice.

The Effect of Compounds 6 and 7 on Body Weight Gain in High Fat Fed C57BL/6J Mice C57BL/6J mice were acclimatized in their new environment for 4 weeks with free access to a high fat diet and water. Mice were then treated twice daily s.c. with compound 6 and compound 7 (at the two doses: 0.5 and 5 nmol/kg) or vehicle for 10 days. Throughout the study, body weights were recorded daily and used to administer the body weight-corrected doses of peptide (FIG. 6). Mice were sacrificed by cervical dislocation.

Compound 6 and compound 7 significantly decreased body weight gain at both doses (0.5 and 5 nmol/kg) in high fat fed C57BL/6J mice.

The invention claimed is:

1. A compound having the formula

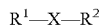

wherein

R$^1$ is H, C$_{1-4}$ alkyl, acetyl, formyl, benzoyl or trifluoroacetyl;

R$^2$ is OH or NH$_2$; and

X is a peptide which has the formula I:
HSQGTFTSDYSKYLDE-K(Hexadecanoyl-isoGlu)-RAKDFIEWLLSA (SEQ ID NO:9)

or a pharmaceutically acceptable salt thereof.

2. A compound according to claim 1 wherein R$^1$ is H.

3. A compound according to claim 1 wherein R$^2$ is NH$_2$.

4. A compound according to claim 1, wherein said compound is
H-HSQGTFTSDYSKYLDE-K(Hexadecanoyl-isoGlu)-RAKDFIEWLLSA-NH$_2$ (SEQ ID NO:9),
or a pharmaceutically acceptable salts thereof.

5. A composition comprising a compound according to claim 1, or a salt or derivative thereof, in admixture with a carrier.

6. A composition according to claim 5 wherein the composition is a pharmaceutically acceptable composition, and the carrier is a pharmaceutically acceptable carrier.

7. A method of preventing weight gain or promoting weight loss in an individual in need thereof, said method comprising administering to said individual a therapeutically effective amount of a compound according to claim 1.

8. A method of lowering circulating LDL levels, and/or increasing HDL/LDL ratio in an individual in need thereof, said method comprising administering to said individual a therapeutically effective amount of a compound according to claim 1.

9. The method according to claim 8 wherein the compound is administered as part of a combination therapy together with an agent for treatment of obesity, dyslipidemia or hypertension.

10. The method according to claim 9, wherein the agent for treatment of obesity is a glucagon-like peptide receptor 1 agonist, peptide YY receptor agonist or analogue thereof, cannabinoid receptor 1 antagonist, lipase inhibitor, melanocortin receptor 4 agonist, or melanin concentrating hormone receptor 1 antagonist.

11. The method according to claim 9 wherein the agent for treatment of hypertension is an angiotensin-converting enzyme inhibitor, angiotensin II receptor blocker, diuretic, beta-blocker, or calcium channel blocker.

12. The method according to claim 9 wherein the agent for treatment of dyslipidaemia is a statin, a fibrate, a niacin or a cholesterol absorption inhibitor.

13. A method of treating a condition caused or characterised by excess body weight in an individual in need thereof, said method comprising administering to said individual a therapeutically effective amount of a compound according to claim 1.

14. The method according to claim 13, wherein the condition is obesity, morbid obesity, morbid obesity prior to surgery, obesity linked inflammation, obesity linked gallbladder disease, obesity induced sleep apnea, hypertension, atherogenic dyslipidimia, atherosclerois, arteriosclerosis, coronary heart disease, peripheral artery disease, stroke or microvascular disease.

15. The method according to claim 14 wherein the compound is administered as part of a combination therapy together with an agent for treatment of obesity, dyslipidemia or hypertension.

16. The method according to claim 15, wherein the agent for treatment of obesity is a glucagon-like peptide receptor 1 agonist, peptide YY receptor agonist or analogue thereof, cannabinoid receptor 1 antagonist, lipase inhibitor, melanocortin receptor 4 agonist, or melanin concentrating hormone receptor 1 antagonist.

17. The method according to claim 15 wherein the agent for treatment of hypertension is an angiotensin-converting enzyme inhibitor, angiotensin II receptor blocker, diuretic, beta-blocker, or calcium channel blocker.

18. The method according to claim 15 wherein the agent for treatment of dyslipidaemia is a statin, a fibrate, a niacin or a cholesterol absorption inhibitor.

19. The method according to claim 13 wherein the compound is administered as part of a combination therapy together with an agent for treatment of obesity, dyslipidemia or hypertension.

20. The method according to claim 19, wherein the agent for treatment of obesity is a glucagon-like peptide receptor 1 agonist, peptide YY receptor agonist or analogue thereof, cannabinoid receptor 1 antagonist, lipase inhibitor, melanocortin receptor 4 agonist, or melanin concentrating hormone receptor 1 antagonist.

21. The method according to claim 19 wherein the agent for treatment of hypertension is an angiotensin-converting enzyme inhibitor, angiotensin II receptor blocker, diuretic, beta-blocker, or calcium channel blocker.

22. The method according to claim 19 wherein the agent for treatment of dyslipidaemia is a statin, a fibrate, a niacin or a cholesterol absorption inhibitor.

* * * * *